United States Patent
Johannison et al.

(10) Patent No.: US 11,559,441 B2
(45) Date of Patent: Jan. 24, 2023

(54) METHOD FOR MANUFACTURING A WOUND DRESSING AND A WOUND DRESSING

(71) Applicant: Mölnlycke Health Care AB, Gothenburg (SE)

(72) Inventors: Ulf Johannison, Landvetter (SE); Steen Jörgensen, Gothenburg (SE); Magnus Paledzki, Brunswick, ME (US)

(73) Assignee: Mölnlycke Health Care AB, Gothenburg (SE)

( * ) Notice: Subject to any disclaimer, the term of this patent is extended or adjusted under 35 U.S.C. 154(b) by 676 days.

(21) Appl. No.: 16/495,232

(22) PCT Filed: Mar. 21, 2018

(86) PCT No.: PCT/EP2018/057176
§ 371 (c)(1),
(2) Date: Sep. 18, 2019

(87) PCT Pub. No.: WO2018/172414
PCT Pub. Date: Sep. 27, 2018

(65) Prior Publication Data
US 2020/0030153 A1    Jan. 30, 2020

(30) Foreign Application Priority Data

Mar. 22, 2017   (EP) ..................... 17162329

(51) Int. Cl.
*A61F 13/00* (2006.01)
*A61F 13/02* (2006.01)
(Continued)

(52) U.S. Cl.
CPC ........ *A61F 13/0289* (2013.01); *A61L 15/425* (2013.01); *A61L 24/0026* (2013.01);
(Continued)

(58) Field of Classification Search
None
See application file for complete search history.

(56) References Cited

U.S. PATENT DOCUMENTS 3,214,502 A   10/1965   Schaar
4,758,297 A    7/1988   Calligarich
(Continued)

FOREIGN PATENT DOCUMENTS

CN        1115170 C     7/2003
CN      100381277 C     4/2008
(Continued)

OTHER PUBLICATIONS

International Search Report and Written Opinion dated Apr. 19, 2018 by the International Searching Authority for International Application No. PCT/EP2018/057176, filed on Mar. 21, 2018 and published as WO 2018/172414 on Sep. 27, 2018 (Applicant—Mölnlycke Health Care AB) (13 Pages).
(Continued)

*Primary Examiner* — Kim M Lewis
(74) *Attorney, Agent, or Firm* — Ballard Spahr LLP

(57) ABSTRACT

A method for manufacturing a wound dressing having a substrate, and a wound dressing manufactured by such a method are described. The method has a step of providing a sacrificial layer of material to be perforated by means of a hot pin perforator, in order to remove any molten residues on the heated pins of the hot pin perforator, before the same pins are used to make holes in the substrate. The presented method is cost effective, robust and reduces the risk of contaminating substances being embedded in the substrate during the hole making process.

19 Claims, 4 Drawing Sheets

(51) Int. Cl.
*A61L 15/42* (2006.01)
*A61L 24/00* (2006.01)
*A61L 24/04* (2006.01)
*B26D 7/10* (2006.01)
*B26F 1/24* (2006.01)

(52) U.S. Cl.
CPC .............. *A61L 24/046* (2013.01); *B26D 7/10* (2013.01); *B26F 1/24* (2013.01)

(56) References Cited

U.S. PATENT DOCUMENTS

| | | | |
|---|---|---|---|
| 5,735,984 A | 4/1998 | Hoff et al. | |
| 5,810,756 A * | 9/1998 | Montecalvo | A61F 13/0276 602/57 |
| 5,965,154 A * | 10/1999 | Haralambopoulos | A61K 9/703 424/447 |
| 6,051,747 A * | 4/2000 | Lindqvist | A61F 13/0209 602/41 |
| 2004/0161586 A1 * | 8/2004 | Cree | B29C 59/04 428/137 |
| 2007/0029694 A1 | 2/2007 | Cree et al. | |
| 2009/0233046 A1 * | 9/2009 | Iulianetti | B32B 5/26 428/137 |
| 2017/0165862 A1 | 6/2017 | Slama et al. | |

FOREIGN PATENT DOCUMENTS

| | | |
|---|---|---|
| CN | 103921447 A | 7/2014 |
| CN | 204076318 U | 1/2015 |
| CN | 105813814 A | 7/2016 |
| EP | 0855921 B1 | 1/2002 |
| GB | 1552491 A | 9/1979 |
| GB | 2313338 A | 11/1997 |
| WO | WO 1997/42985 | 11/1997 |
| WO | WO-99/055532 A1 | 11/1999 |
| WO | WO 2004/058121 | 7/2004 |
| WO | WO-2010/061228 A1 | 6/2010 |

OTHER PUBLICATIONS

European Search Report and Written Opinion dated Sep. 4, 2017 by the European Patent Office for EP Application No. 17162329.1, filed on Mar. 22, 2017 and published as EP 3378450 A1 on Sep. 26, 2018 (Applicant—Mölnlycke Health Care AB) (11 Pages).

\* cited by examiner

METHOD FOR MANUFACTURING A WOUND DRESSING AND A WOUND DRESSING

CROSS-REFERENCE TO RELATED APPLICATIONS

This application is a U.S. National Phase Application of International Application No. PCT/EP2018/057176, filed Mar. 21, 2018, which claims priority to European Application No. 17162329.1, filed Mar. 22, 2017, each of which are hereby incorporated by reference in their entirety.

TECHNICAL FIELD OF THE INVENTION

The present invention relates to the field of wound dressings, and in particular to a method for manufacturing a wound dressing. The present invention also relates to a wound dressing manufactured according to said method.

BACKGROUND

In the medical field it is known that wound sites are to be covered in order to protect the wound sites from ingress of foreign material, i.e. to keep it clean, but also to collect or absorb exudate from the wound site. Therefore, a simple cotton bundle arranged to absorb the exudate is often seen as a traditional wound dressing.

However, the wound healing process is more complex and there have been many advancements in the technical field to improve and speed up this healing process. Generally, a wound healing process can in principle be subdivided into three phases. Firstly, the wound is cleaned, followed by the formation of new tissue, after which the restored tissues stabilize during a final maturing phase while developing a less brittle and more elastic structure. The regeneration phase involves the growth of capillaries, fibroblasts and epithelium into the wound site for building up new tissue. The newly formed tissue is extremely delicate and supersensitive to external influences. However, it is known that in order to attain the most favourable conditions for wound healing, the wound should be kept moist but free of excess wound exudate during this phase of wound repair.

An example of such a wound dressing which aims to improve the healing process is commercially available by the present applicant, Mölnycke Health Care AB from Göteborg, Sweden, and is for example described in European Patent No. 0 855 921 B1, incorporated herein by reference.

Nevertheless, there is still a need in the industry for improvements, and particularly relating to the manufacturing of such wound dressings. In more detail, the wound dressings generally include some sort of absorbing layer, which can be made of some porous material, such as e.g. polyurethane foam, in order to absorb the exudate originating from the wound. Moreover, in cases with large amounts of wound exudate or highly viscous wound exudate, the naturally occurring pores may be insufficient for proper absorption. Instead, one must increase the open surface area (may be referred to as open area) by creating a pattern of holes in the foam material which are significantly larger than the pores or cells of the foam material.

These holes can be made by using a type of heated pin technology (may also be referred to as hot needle technology). Typically, a roller of heated pins is rolled on the absorbent foam layer such that the heated pins are introduced into the material in order to create the holes in a melting process.

A general drawback associated with the heated pin technology is that the heated pins are contaminated with residual material adhering thereto as a result of the pins having formed holes in the absorbent foam material. There is therefore a risk of residues being introduced into the absorbent foam material in a subsequent perforating operation, thereby contaminating the absorbent foam layer.

As a remedy to problems associated with contaminated pins, GB 1 552 491 proposes a manufacturing method for perforating a foam synthetic thermoplastic plastics sheet, in which the residues are burnt off from the heated pins, by means of a gas burner, after each perforating operation. The cleaning of the pins is performed at a position which is opposite the perforation of the foam plastics sheet, i.e. on the opposite side of the heated pin roller. However, these types of setups with auxiliary heating elements often decrease the overall process speed and simultaneously increase complexity and costs of the whole process.

However, there is still a need in the industry for improvements of the manufacturing process for wound dressings. More specifically, there is need for a method for manufacturing wound dressings which is less complex and at the same cost effective and time efficient.

SUMMARY OF THE INVENTION

It is therefore an object of the present invention to provide a method for manufacturing a wound dressing which alleviates all or at least some of the above-discussed drawbacks of the presently known systems.

This object is achieved by means of a method for manufacturing a wound dressing as defined in the appended claims.

The present invention is based on the realization that a layer of material which will not form a part of the end product, may be used to "clean" the heated pins of a hot pin perforator, whereby many of the associated problems with contaminants embedded in the resulting wound dressing are at least partly alleviated.

According to a first aspect of the present invention, there is provided a method for manufacturing a wound dressing having a substrate, the method comprising:
providing a hot pin perforator having an array of heated pins;
providing a sacrificial layer of material adapted to be perforated by the heated pins;
perforating the sacrificial layer with the heated pins;
making holes in the substrate with the heated pins of the hot pin perforator.

The inventive method is not only more cost effective per manufactured unit but it also allows for a higher production rate, all while the resulting product (the wound dressing) still complies will regulatory requirements for medical devices in terms of levels of contaminating substances embedded in the substrate. The produced wound dressing has a substrate (may also be referred to as a substrate layer) with holes open out to the side of the substrate that lies proximal to the wearer's skin when the dressing is used. It is readily understood by the skilled artisan that the wound dressing is applicable for other purposes than solely for absorption of wound exudate. Thus, the term is to be understood to encompass interface dressings and wound preventing dressings, for example, it may also be applied onto healthy skin in order to absorb sweat or to provide pressure relief. Stated differently, the wound dressing may be used as an interface dressing or wound preventing dressing, e.g. for preventing pressure ulcers.

The substrate may comprise an absorbent material, and the absorbent material may e.g. be a polymeric foam such as a hydrophilic polyurethane foam, a non-woven material, fibrous material such as fibrous hydrophilic polymeric material, gel forming fibers, hydrogel, a matrix containing hydrocolloids, woven and knitted fibers, or combinations thereof.

In more detail, the absorbent material can be characterized by a free swell absorptive capacity, corresponding to the maximum absorptive capacity, of at least 3 times its own weight as measured by EN 13726-1:2002. In accordance with the present invention, the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

Preferably, the term "hydrophilic" refers to the water-permeability property of a material or the water-attracting property of a molecule. In the context of a material with pores (such as, for example, open-cell foams) or materials with through-holes, such a material is "hydrophilic" if the material takes up water. In the context of a material without pores or any through-holes, such a material is considered "hydrophilic" if it does not resist the flow of water into or through the material. For example, hydrophilicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

In accordance with an embodiment of the invention, the substrate is, or is comprised in, a layer, i.e. the substrate may be a substrate layer. The thickness of the substrate layer is then at least 250 µm, preferably at least 1 mm, more preferably at least 3 mm. A "layer" as used in accordance with the present invention should be understood to have a continuous extension in one plane (x and y direction) and a thickness perpendicular to said plane (z direction).

The step of making holes in the substrate includes making through holes and/or making blind holes in the substrate. A blind hole is in the present context to be understood as a hole that has a specific depth without breaking through to the other side of the material, as opposed to a through hole which goes all the way through the material. In the following, the step of making holes may be referred to as a piercing or hole making operation.

Further, the present inventors realized that conventional production methods for manufacturing wound dressings are prone to some general drawbacks. For example, the commonly used laser technology to pierce a surface of the substrate (i.e. to make holes in the substrate) is inherently a slow and costly process. On the other hand, even if, heated pin technology in its most basic form provides advantages in terms of speed and cost, it proved to be problematic to avoid contamination of the absorbent material in the form of residues from a piercing operation being introduced into the substrate in the subsequent piercing operations. Thus, making it unsuitable for manufacturing of medical devices such as wound dressings. Even though the residues could potentially be burned off if the time duration between each piercing operation was long enough to allow the residues to evaporate, it would be detrimental to the production speed.

Also, increasing the operating temperature or utilizing auxiliary equipment to "burn off" the residues at a faster rate either increased the cost and complexity of production, or was practically impossible due to the material properties of the heated pin perforator and the substrate. More specifically, the operating temperature of the hot pin perforator cannot be allowed to exceed a certain threshold. Thus, by suitably positioning a sacrificial layer of material to be perforated/penetrated by the heated pins before the pins are introduced into the substrate, the issues related to contaminating residues are significantly reduced.

In more detail, the perforation of the sacrificial layer may be understood as a "cleaning" operation, where any molten residues stuck to the heated pins from a perforation operation are stripped or scraped off by the sacrificial layer when the heated pins are pushed therethrough. The perforation of the sacrificial layer may be performed as process step that is separate from the making of the holes in the substrate, or alternatively, the perforation of the sacrificial layer may be done in one and the same step as the making of the holes in the substrate. These two alternatives will however be further elucidated in the detailed description with reference to the appended drawings. The sacrificial layer may be discarded in a subsequent process step.

The sacrificial layer may in some embodiments of the present invention be made from aluminium (e.g. a thin aluminium foil) or thin paper materials. However, the sacrificial layer may alternatively be made from nonwoven or plastic film, such as e.g. polyester or polypropylene. Preferably, the sacrificial layer has a melting point temperature at or below the operating temperature of the hot pin perforator. By having a meltable/fusible material in the sacrificial layer, i.e. melting point below the operating temperature of the hot pin perforator, the perforations made by the heated pins will be distinct and well-defined with reduced risk of cracking in the layer which increases the amount of residue caught by the sacrificial layer, and thereby the efficiency of the setup, when it is perforated by the heated pins.

Further, in accordance with an embodiment of the present invention, the hot pin perforator is arranged so that the heated pins perforate the sacrificial layer before reaching a proximal surface of the substrate in order to remove residues on the heated pins before they are brought in contact with the substrate.

It should be understood that even if it is expressed that the heated pins perforate the sacrificial layer "before" they are introduced into the substrate; the term is to be understood to encompass a scenario where the heated pins perforate the sacrificial layer "after" a perforation operation in the substrate. This depends on one's point of view, and the latter scenario can be understood as that the heated pins perforate the sacrificial layer "before" a subsequent hole making operation in the substrate. The term "before" was selected without prejudice since it was deemed to be clearer in relation to the effect, i.e. that the pins are "cleaned" before every subsequent hole making process, but as mentioned, it may equivalently be understood as the pins being "cleaned" after a hole making process.

For example, if a spiked pin roller is utilized as a hot pin perforator and the substrate is positioned at a 6 o'clock position relative to the roller, the sacrificial layer can be arranged to be perforated by the heated pins at a 3 o'clock position, 12 o'clock position, 9 o'clock position or even a 6 o'clock position relative to the roller, however, in the 6 o'clock position the sacrificial layer is to be arranged between the substrate and the roller.

Further, in accordance with an embodiment of the invention, the array of heated pins comprises a pin density in the range of 3-10 pins per cm$^2$, preferably in the range of 4-8 pins per cm$^2$, and more preferably in the range of 4-7 pins per cm$^2$. Naturally, the pin density directly translates to the resulting hole density in the substrate, i.e. to the number of holes per cm$^2$ on the proximal surface of the substrate. The pin diameter may for example be in the range of 1-5 mm, preferably in the range of 1.5-4 mm and more preferably in the range of 2-3.5 mm. The resulting hole diameter depends on various factors, such as pin shape and penetration depth, pin diameter, operating temperature of the hot pin perforator (i.e. temperature of the heated pins) and process speed (i.e. how long time the pins are in contact with the substrate). Nevertheless, in accordance with an embodiment of the invention, the hot pin perforator is arranged such that the diameter of the resulting holes in the substrate is in the range of 0.2-4 mm or such that an open surface area of the substrate is in the range of 0.1-20%, depending on the intended application for the end product. As previously mentioned, in cases of wounds with amounts of viscous exudate, the naturally occurring pores may be insufficient for proper absorption. Instead, one must increase the open area by creating a pattern of holes in the substrate which are larger than the pores or cells of the substrate.

Even further, in accordance with another embodiment of the present invention, the heated pins have a temperature at or above the melting point of the substrate. For example, the temperature of the heated pins may be in the range of 100% to 200% of the melting point temperature of the substrate. Thus, the operating temperature of the hot pin perforator is preferably selected based on the material choice for the substrate, but may for example be in the range of 200° C. to 600° C., preferably in the range of 250° C. to 500° C., such as e.g. 300°, 350° C., 400° C. or 450° C. It is advantageous to arrange the heated pins to have a temperature in the upper end of the aforementioned range, i.e. in the range of 150% to 200% of the melting point of the substrate, in order to be able to increase process speed. Having a higher pin temperature results in a faster hole formation in the substrate and therefore increased throughput and yield.

Moreover, in accordance with another embodiment of the present invention the hot pin perforator comprises a roller having a plurality of heated pins mounted on an outer surface thereof. Stated differently, the roller may be understood as a cylindrical body having a plurality of heated pins extending in a radial direction from the enveloping surface of the cylinder. The hot pin perforator in the form of a roller has the advantages of being of a simple and robust construction which is easy to maintain.

However, the hot pin perforator may also in an alternative embodiment be in the form of a punch which can be hydraulically, pneumatically or electrically actuated. The punch may thus comprise a plate having a number of heated pins protruding therefrom which are subsequently actuated towards and through the sacrificial layer in order to make holes in the substrate, in a press-type configuration.

Furthermore, in accordance with yet another embodiment of the present invention, the method further comprises providing a supporting surface for the substrate on the opposite sides of the sacrificial layer and the substrate relative to the hot pin perforator, such that the hot pin perforator and the supporting surface form a gap through which the substrate and sacrificial layer passes. The supporting surface may for example be the outer surface of a counter roller. In fact, the general outlay of the manufacturing system may be in the form of a rolling conveyor system.

Further, by providing a supporting surface to serve as a base or support for the substrate during the piercing or hole making operation, the depth of the holes can be controlled in an accurate manner. Stated differently, by controlling the size of the gap formed between the hot pin perforator and the supporting surface, i.e. the distance between the two, the resulting hole depth can be controlled.

Moreover, the supporting surface may comprise a pliant/soft or resilient material, such as e.g. silicone, rubber, or the like. By having a pliant supporting surface, the risk of damaging the tips of the hot pins during a piercing operation is reduced whereby the lifetime of the hot pin perforator is increased. For example, in the case where the supporting surface is in the form of a counter roller, the outer surface of the counter roller may comprise a silicone or rubber sheet applied thereon.

Yet further, in accordance with yet another embodiment of the present invention, the step of providing a sacrificial layer of material comprises positioning the sacrificial layer of material between the hot pin perforator and the substrate. By positioning the sacrificial layer between the hot pin perforator and the substrate, the manufacturing complexity is decreased since the "cleaning" of the heated pins and the hole making operation can be performed in one and the same step. Accordingly, if the substrate and the sacrificial layer are in the form of rolled up sheets arranged on conveyor rollers, the two layers can be rolled out in a parallel fashion so that they both pass by the hot pin perforator in a rolling-conveyor-type of setup, thereby increasing production speed. Subsequently, the substrate can be transported continuously for any potential after treatment operations, while the sacrificial layer can separately be transported for discarding.

The mentioned after-treatment may for example be applying an adhesive layer or adhesive coating. Thus, in accordance with another embodiment of the present invention, the method further comprises applying an adhesive layer/coating onto the proximal surface of the substrate. The proximal surface of the substrate is to be understood as that side or surface of substrate which faces the hot pin perforator when the holes are made. This is the same surface which lies proximal to the wearer's skin when the dressing is worn, which in this embodiment is gel coated. The adhesive layer may comprise a silicone based adhesive, acrylic adhesive, or a pressure-sensitive adhesive (PSA) holtmelt. The adhesive layer preferably has hydrophobic properties in order to prevent spontaneous reflux of absorbed fluid to the skin or the wound when the wound dressing is worn. This increases patient comfort and reduces the risk of deteriorating the healing process by damaging wound tissue during removal or change of the wound dressing.

The wound tissue would also be mechanically damaged in connection with removal and change of dressing. To avoid this, it is advantageous if the dressing applied to the wound does not to get stuck in dried-up wound exudate, or in any coagulum possibly formed. This is accordingly achieved by the adhesive layer which will act as a spacer layer between the skin of the wearer and the substrate, the adhesive slightly extends into the holes and covers the circumferential rims of the holes without blocking the holes (or blocking any naturally occurring pores). Thereby, preventing contact between the substrate and the skin, yet allowing wound exudate to be drawn into the substrate. Naturally, some holes or pores may be blocked due to manufacturing tolerances, however, at least some of the produced holes and naturally occurring pores remain open towards the proximal side of the substrate.

Further, in accordance with yet another embodiment of the present invention, the step of applying an adhesive layer onto a perforated surface of the substrate comprises applying a sheet of transfer paper comprising an adhesive mixture onto a proximal surface of the substrate, curing the adhesive mixture, and removing the transfer paper thereby leaving an adhesive layer on the proximal surface of the substrate. Hereby a simple and efficient means for applying an adhesive layer onto the proximal surface, i.e. perforated surface, of the substrate is presented. The thickness of the resulting adhesive layer is preferably in the range of 0.1 to 2.0 mm.

Further, in accordance with yet another embodiment of the present invention, the method further comprises applying a backing layer onto a distal surface of the substrate, wherein the backing layer comprises a liquid impervious material. The distal surface is accordingly to be understood as the side of the substrate that in use lies distal from the wearer's skin. Stated differently, the distal surface is the surface which faces away from the hot pin perforator during the piercing or hole making operation. By coating the distal surface with a backing layer, the risk of fluid absorbed by the substrate leaking out is reduced. The backing layer may for example comprise a thermoplastic polymer, and be in the form of a film, such as e.g. a polyurethane film.

Suitable backing layer are, for example, films, foils, foams, or membranes. Furthermore, the backing layer may have a thickness in the range from ≥5 μm up to ≤80 μm, particularly preferred in the range from ≥5 μm up to ≤60 μm, and particularly preferred in the range from ≥10 μm up to ≤30 μm and/or that the backing layer has an elongation at break of more than 450%. The backing layer is preferably pervious to water vapour.

According to another aspect of the present invention, there is provided a wound dressing manufactured by a method according to any one of the embodiments discussed with respect to the preceding aspect of the present invention.

In accordance with an embodiment of the invention, the substrate of the wound dressing comprises holes having a diameter of the resulting holes in the range of 0.2-4 mm or such that an open surface area of the substrate is in the range of 0.1-20%

These and other features and advantages of the present invention will in the following be further clarified with reference to the embodiments described hereinafter.

BRIEF DESCRIPTION OF THE DRAWINGS

For exemplifying purposes, the invention will be described in close detail in the following with reference to embodiments thereof illustrated in the attached drawings, wherein.

DETAILED DESCRIPTION

In the following detailed description, some embodiments of the present invention will be described. However, it is to be understood that features of the different embodiments are exchangeable between the embodiments and may be combined in different ways, unless anything else is specifically indicated. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

Figure 1:
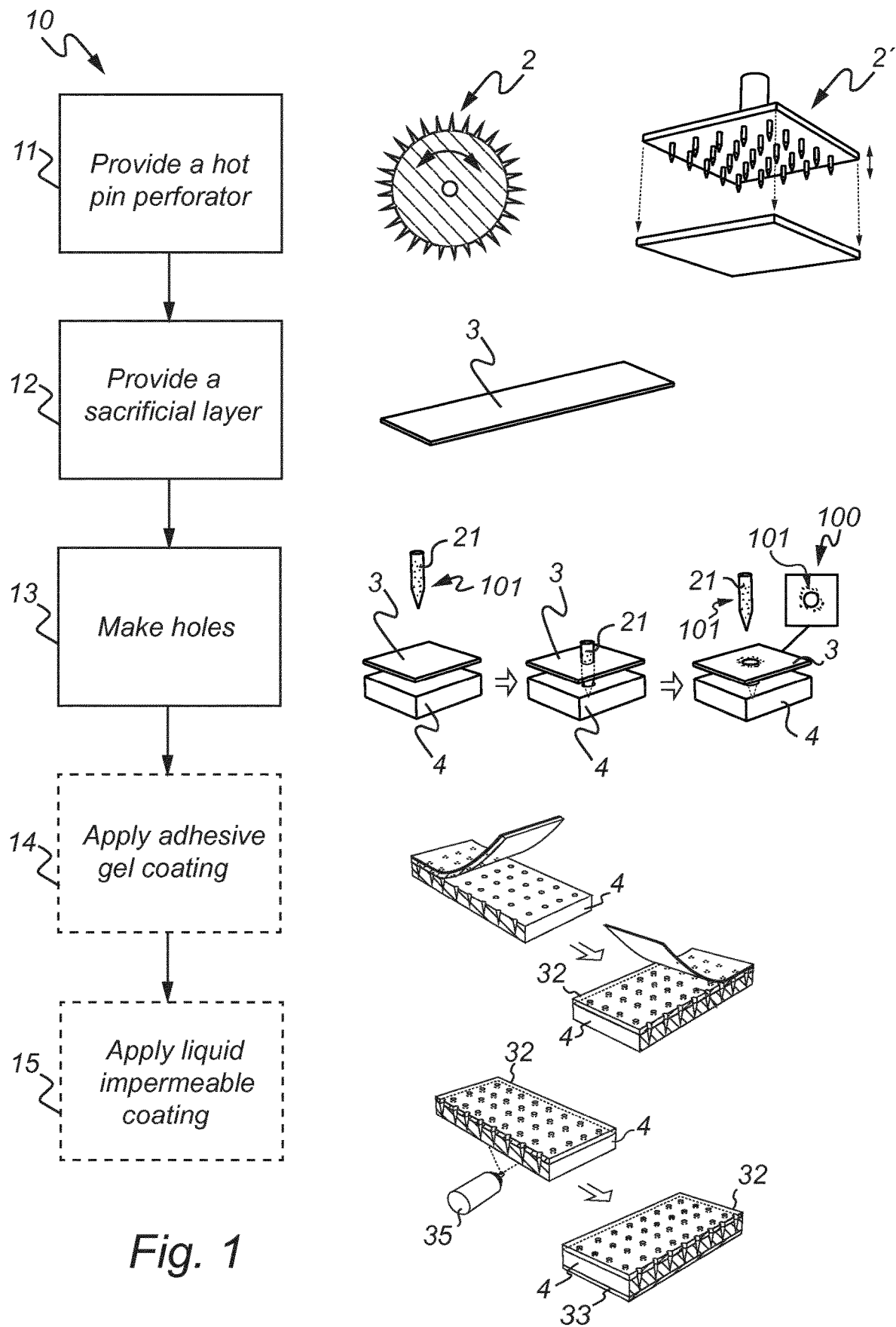
FIG. 1 illustrates a schematic flow chart representation of a manufacturing method in accordance with an embodiment of the present invention.

FIG. 1 shows a schematic flow chart representation of a method 10 for manufacturing a wound dressing having a substrate 4 in accordance with an embodiment of the present invention. The inventive method is particularly suitable for making holes in open cell absorbent foam materials, thus, the substrate 4 may for example be an absorbent foam material with open pores or cells, such as e.g. a polyurethane foam produced from a composition comprising a prepolymer based on: hexamethylene diisocyante (HDI), toluene diisocyanate (TDI), or methylene diphenyl diisocyanate (MDI). The substrate is preferably selected to have a pore size in the range of 30 μm to 1000 μm. However, as previously mentioned the absorbent material may also be an absorbent non-woven material such as e.g., poly(vinyl alcohol) fibres, carboxymethyl cellulose (CMC) fibres, or any other equivalent and suitable material.

The substrate 4 is here in the form of a substrate layer 4 preferably having a thickness in the range of 0.25-10 mm, such as in the range of 2-8 mm, depending on requirements in terms of absorption capacity and flexibility. However, in other embodiments of the invention (not shown), the substrate 4 comprises a first sublayer and a second sublayer. Stated differently, the substrate 4 may comprise a plurality of superimposed sublayers.

Firstly, a hot pin perforator 2, 2' is provided in step 11. The hot pin perforator may for example be roller 2 having a plurality of heated pins arranged on an outer surface thereof (may also be called a spiked pin roller 2) as indicated in the leftmost illustration to the right of the box indicating step 11. However, the hot pin perforator may also be in the form of a pressing arrangement 2', as indicated in the rightmost illustration next to the box indicating step 11. Further, a sacrificial layer 3 of material adapted to be perforated by the heated pins is provided in step 12. The sacrificial layer 3 is preferably made of a material that has a melting point temperature below the operating temperature of the hot pin perforator 2, 2', i.e. below the temperature of the heated pins. The sacrificial layer 3 may for example be made from nonwoven or plastic film, such as e.g. polyester or polypropylene, alternatively the sacrificial layer may be made from thin paper materials. The sacrificial layer 3 may have a thickness in the range of 50 μm to 200 μm, or if the sacrificial layer 3 is in the form of a nonwoven or thin paper material the thickness may be in the range of 50 g/m² to 200 g/m².

Moving on, holes are made in step 13 in the substrate 4. In more detail, the holes are made in a piercing operation in which the heated pins 21 of the hot pin perforator 2, 2' are brought in contact with a proximal surface 61 of the substrate 4 and allowed to penetrate into the material, effectively melting a hole into the material. However, the hot pin perforator 2, 2' is arranged such that the heated pins 21 perforate the sacrificial layer 3 before reaching the proximal surface 61 of the substrate 4 (as exemplified in the illustrations to the right of the box indicating step 13). Although the illustrations in FIG. 1 show an example where the sacrificial layer 3 is provided between the heated pin 21 (i.e. the hot pin perforator) and the substrate 4, other arrangements are feasible and will be further discussed in reference to e.g. FIG. 2B. Furthermore, by having a material in the sacrificial layer 3 that slightly melts upon contact with the heated pins 21, i.e. having a melting point below the operating temperature of the hot pin perforator 2, 2', the perforations made by the heated pins 21 will be distinct and well-defined while the risk of cracks or tears in the sacrificial layer 3 is reduced. Consequently, the amount of residue 101 caught by the sacrificial layer 3 increases, and the efficiency of the manufacturing process and particularly the efficiency of the cleaning of the pins 21 by means of the sacrificial layer 3 is increased. The sacrificial layer 3 preferably has a melting point in the range of 30% to 100% of the temperature of the heated pins 21, i.e. 30% to 100% of the operating temperature of the hot pin perforator 2, 2'. For example, if the heated pins have a temperature of 400° C., the sacrificial layer 3 is preferably arranged to have a melting point in the range of 120° C. to 400° C.

Moreover, the sequence of figures to the right of box indicating step 13 illustrate an example of the "cleaning process" of the heated pins 21. Firstly, a heated pin 21 with contaminating residual material 101 (residues from a preceding hole making operation) is positioned to make a hole in the substrate. Subsequently the pin 21 is moved towards the substrate 4, through the sacrificial layer 3, in order to make a hole in the substrate 4. Finally, the heated pin 21 is retracted whereby a resulting hole is formed in the substrate 4. As indicated in the rightmost illustration, and particularly in the enlarged view 100, the sacrificial layer 3 has collected or "scraped off" the contaminating residual material 101 from the heated pin 21 during its passage through the sacrificial layer 3. As can also be seen, the heated pin 21 is again contaminated by molten residues from the substrate from the hole making operating (middle illustration). Thus, upon another sequence of making a hole in the substrate, these residues will again be caught by the sacrificial layer 3 when the heated pin 3 perforates an unperforated area of the sacrificial layer 3.

The resulting holes in the substrate 4 are preferably blind holes, but may in some applications be through holes, where in the latter case the heated pins 21 pass all the way through the layer of absorbent foam material 4. A combination of blind holes and through holes is also conceivable, for example, the heated pins 21 of the hot pin perforator 2 may have different lengths.

Further the method 10 comprises the optional steps 14 and 15, in step 14 an adhesive layer 32 is applied onto a proximal surface 61 of the substrate 4, and in step 15 a backing layer 33 is applied onto a distal surface 62 of the substrate 4. More specifically the step of applying a backing layer 33 may include, by means of a coating means 35, coating the distal surface 62 of the substrate 4 with an (acrylic) adhesive in order to subsequently adhere the backing layer 33 to the substrate 4. However, these steps will be further discussed in reference to FIGS. 3 and 4.

Figure 2A:
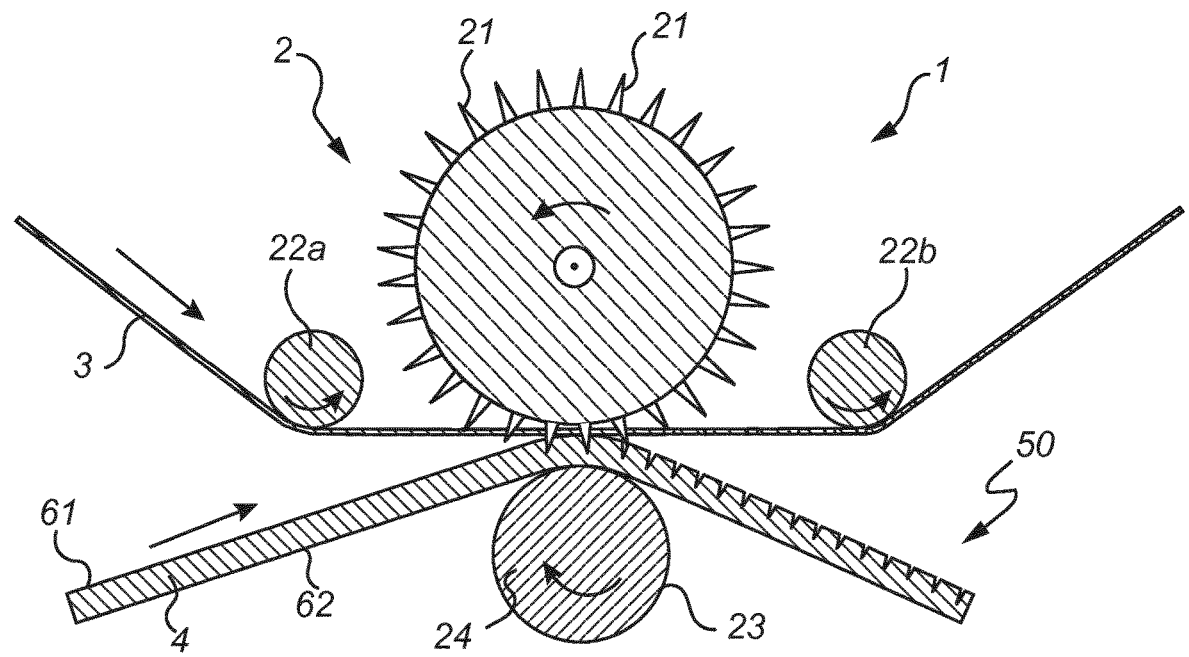
FIG. 2A illustrates a schematic cross-sectional view of a system or apparatus for manufacturing a wound dressing in accordance with an embodiment of the present invention.

FIG. 2A is a schematic cross-sectional view of a manufacturing apparatus or manufacturing arrangement 1 for manufacturing a wound dressing 50 in accordance with an embodiment of the invention. The manufacturing arrangement 1 comprises a hot pin perforator 2, here in the form of a spiked pin roller, having an array of heated pins 21 arranged on an outer surface thereof. The arrangement 1 further has a set of rolling conveyor elements 22a, 22b, 24 in order to bring the substrate 4 and the sacrificial layer 3 in contact with the heated pin 21 of the hot pin perforator 2. The pins may for example be heated by infrared radiation, suitably arranged heating elements, gas burners, etc. Stated differently, the hot pin perforator may comprise any suitable means for heating the pins. The pin temperature, i.e. the operating temperature of the hot pin perforator 2, may for example be in the range of 200° C. to 600° C., though, the temperature is preferably set in relation to the melting point temperature of the substrate. For example, the temperature of the heated pins 21 may be in the range of 100% to 200% of the melting point temperature of the substrate 4.

Further, each of the heated pins 21 may have a length in the range of 1 to 15 mm, preferably in the range of 5 to 10 mm, and a diameter in the range of 1 to 5 mm. The heated pins 21 may have a substantially cylindrical shape with a conical or tapering tip. Also, the pin density of the hot pin perforator 2 is in the range of 3-10 pins per cm², preferably in the range of 4-8 pins per cm², and more preferably in the range of 4-7 pins per cm². The pin density of the hot pin perforate 2, 2' and consequently the resulting hole density and open surface area of the substrate is suitably selected in order to control the flexibility of the resulting dressing, i.e. a higher hole density or larger open surface area will result in a more flexible wound dressing.

In FIG. 2A, the substrate 4 is fed from left to right and in close proximity to the hot pin perforator 2, whereby, due to the rotation of the hot pin perforator 2, the heated pins 21 penetrate into the substrate 4 as indicated in the illustration. The manufacturing arrangement 1 also has a supporting surface 23, here in the form of an outer surface of a counter roller which is included in the conveyor elements 22a, 22b, 24. The counter roller 24 together with the hot pin perforator 2 form a gap through which the substrate 4 passes. The sacrificial layer 3 travels in parallel to the substrate 4, and is also fed, by means of the rolling conveyor elements 22a, 22b, through the gap formed by the hot pin perforator 2 and the counter roller 24. Accordingly, the heated pins 21 first penetrate the sacrificial layer 3 before reaching the proximal surface 61 of the substrate 4. Thus, residues stuck to the heated pins 21 are "scraped" off when the heated pins pass through the sacrificial layer 3. The sacrificial layer 3 can be discarded after it has been perforated. Preferably, the sacrificial layer is made of a material suitable for recycling, such that it can be molten and re-shaped into a thin sheet or layer in order to be used in the inventive manufacturing method again.

Further, by providing a supporting surface 23 onto which the substrate 4 is positioned during the hole making operation, the depth of the holes can be controlled by controlling the distance between the hot pin perforator 2 and the supporting surface 3. However, the substrate 4 can, in alternative embodiments, be transported under tension (not shown), the hole making operation then occurs in free space and no supporting surface 23 needs to be used to press the substrate 4 towards the heated pins 21, thereby alleviating the need for a supporting surface 23.

Even further, the hot pin perforator is preferably arranged to make holes in the substrate at a rate of 1-20 m per minute. The manufacturing rate is biased towards the lower or upper end of the abovementioned range based on the material choice for the substrate. Since the holes are formed in a melting process, a material with a lower melting point can be processed faster, and analogously, a material with a higher melting point requires more time for proper hole formation.

Figure 2B:
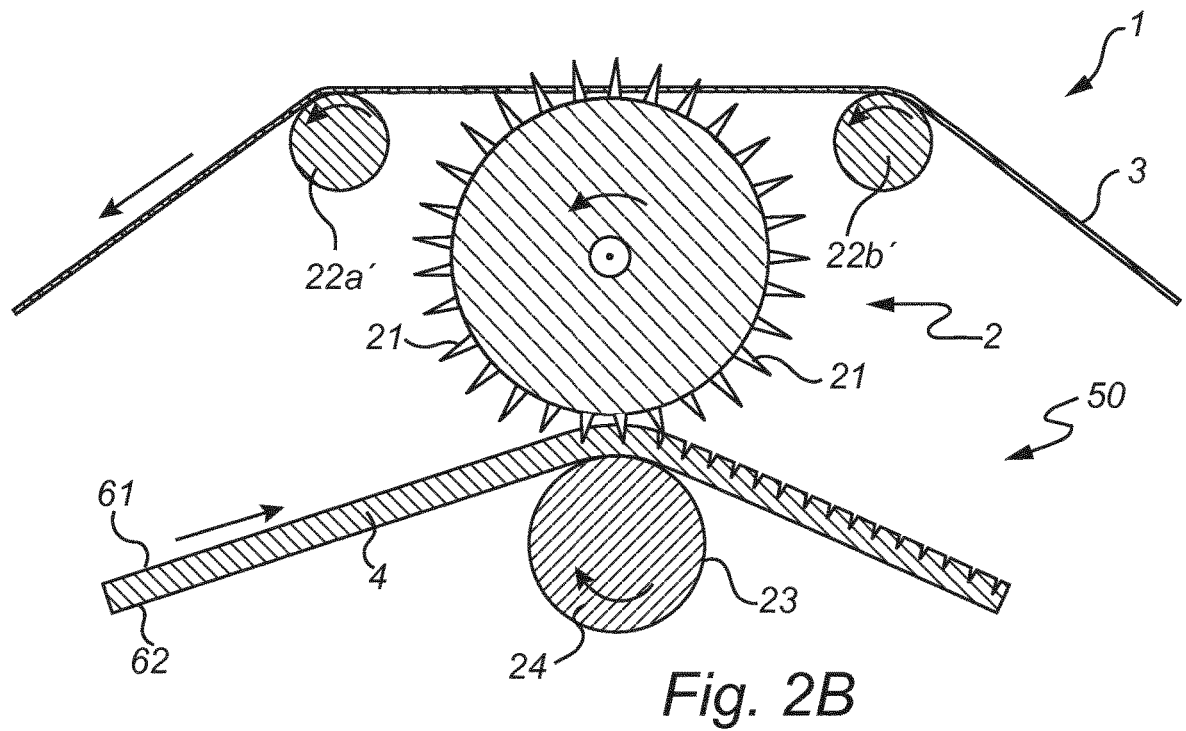
FIG. 2B illustrates a schematic cross-sectional view of a system or apparatus for manufacturing a wound dressing in accordance with another embodiment of the present invention.
Figure 2C:
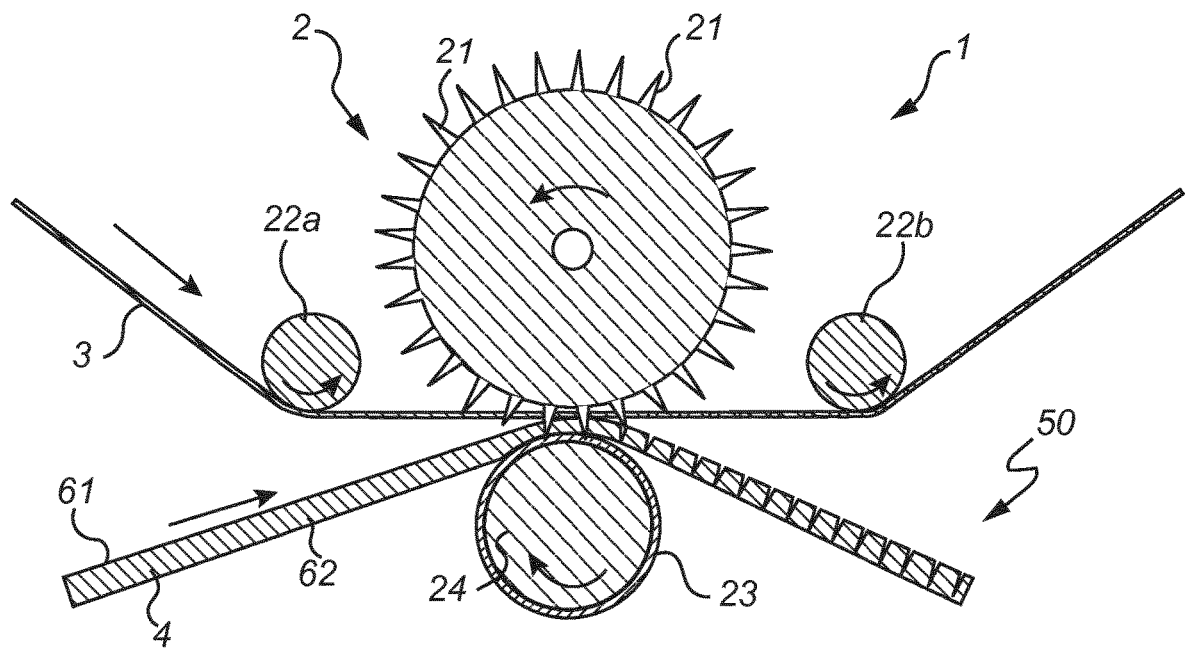
FIG. 2C illustrates a schematic cross-sectional view of a system or apparatus for manufacturing a wound dressing in accordance with yet another embodiment of the present invention.
Figure 2D:
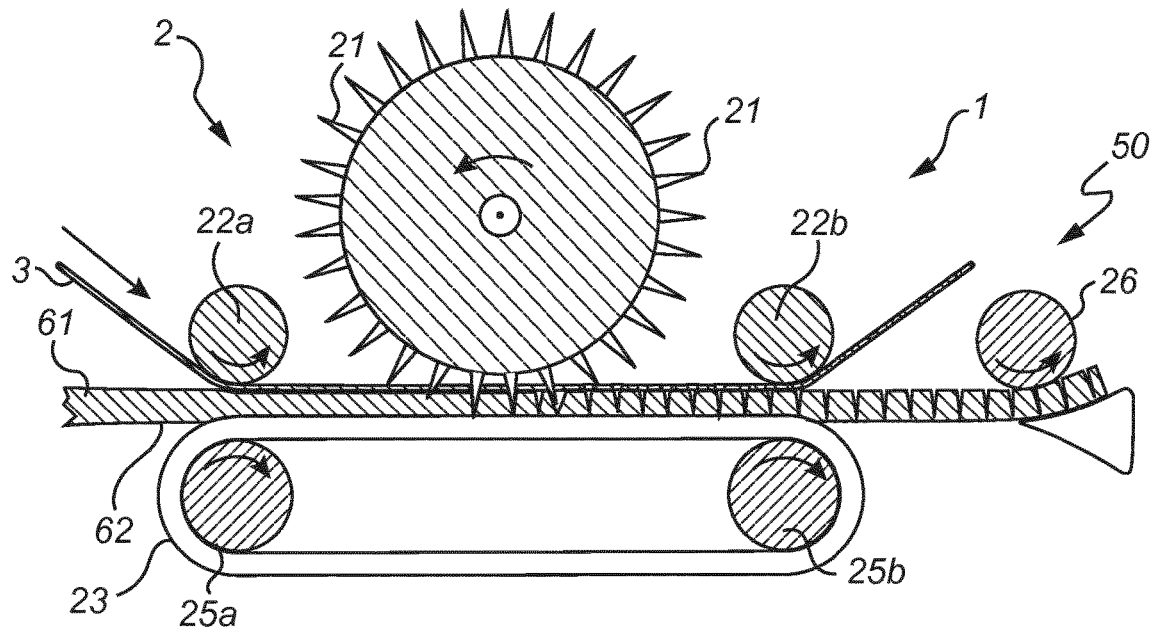
FIG. 2D illustrates a schematic cross-sectional view of a system or apparatus for manufacturing a wound dressing in accordance with yet another embodiment of the present invention.

FIGS. 2B-2D show schematic cross-sectional views of a manufacturing arrangement 1 for manufacturing a wound dressing 50 in accordance with different embodiments of the invention. The operational principle is largely analogous to the one previously described in reference to FIG. 2A, and will for the sake of brevity not be unnecessarily repeated.

However, in the alternative embodiment illustrated in FIG. 2B, the sacrificial layer 3 is positioned at an opposite side of the spiked pin perforator 2 in reference to the substrate 4. Stated differently, the substrate is arranged to be pierced at a 6 o'clock position relative to the hot pin perforator 2, while the sacrificial layer is arranged to be perforated at a 12 o'clock position relative to the hot pin perforator 2 in the illustrated embodiment of FIG. 2B. Accordingly, after the heated pins 21 of the hot pin perforator 2 have pierced through a portion of the substrate 4 there will be some residues of molten material stuck to the outer surface of the heated pins 21. The heated pins 21 are then subsequently cleaned by perforating the sacrificial layer 3 before reaching the proximal surface 61 of the substrate 4 in the subsequent piercing operation.

FIG. 2C shows a manufacturing arrangement 1 for manufacturing a wound dressing 50, where the supporting surface comprises a resilient material, such as e.g. a silicone or rubber layer. In more detail, the counter roller 24 has a resilient sheet arranged about its outer surface. Hereby, the risk of damaging the tips of the heated pins 21 during the piercing operation is reduced, particularly in a scenario, where the manufacturing arrangement 1 is configured to make through holes in the substrate 4. In an alternative embodiment (not shown) the supporting surface 23 may be arranged with indentations or recesses into which the heated pins 21 may protrude during the hole making operation.

In FIG. 2D the manufacturing arrangement 1 comprises a conveyor belt acting as a supporting surface 23. Preferably the conveyor belt comprises a layer of resilient material. The resilient material may for example be a foam material having naturally occurring pores. Supporting surface 23 moves by means of the rolling conveyor elements 25a and 25b. Similar to the arrangement in FIG. 2C, the conveyor belt yields when the heated pins 21 apply a pressing force onto the first substrate 4 during the piercing operation.

Figure 3:
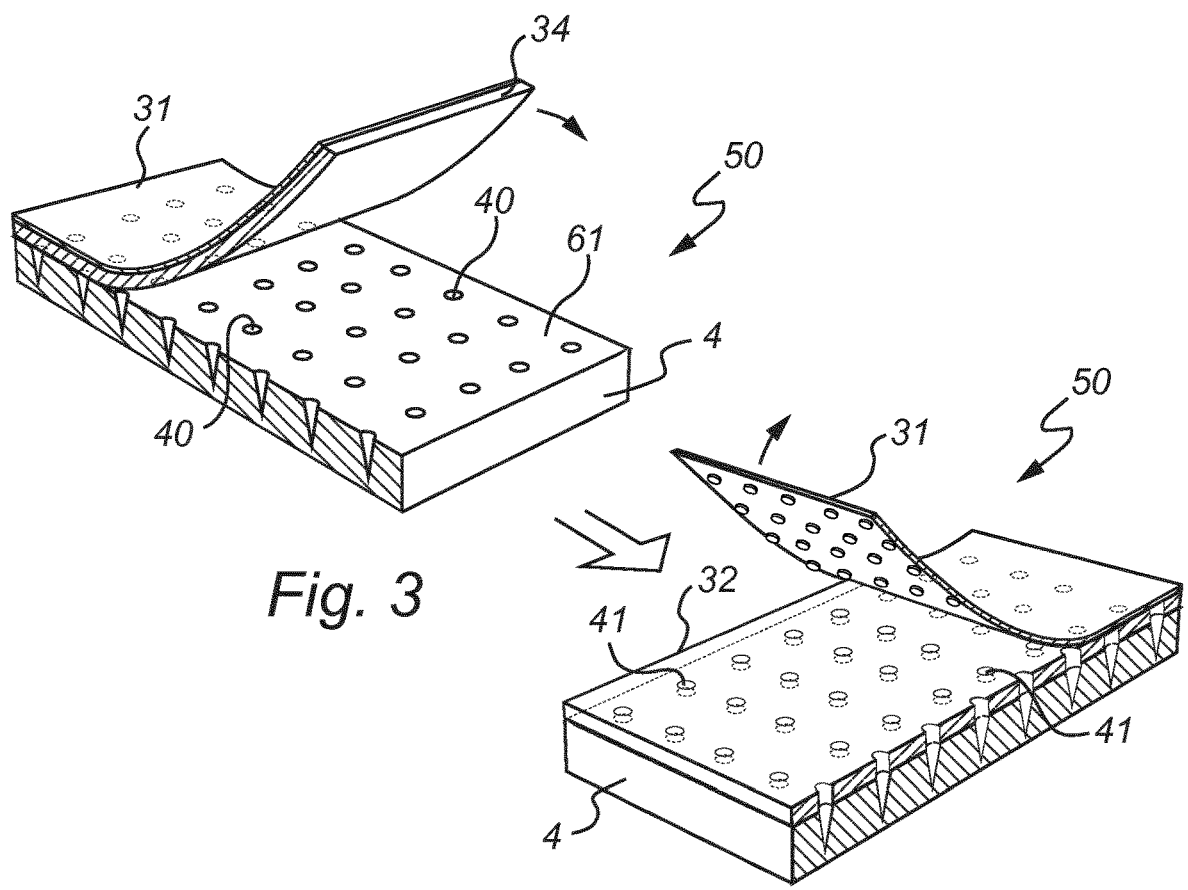
FIG. 3 illustrates a schematic perspective view of a method step for applying a layer of skin adhesive gel onto a proximal surface of a substrate layer, in accordance with an embodiment of the present invention.

FIG. 3 shows a schematic perspective view of a two-step sequence illustrating a method step of coating the proximal surface 61 of the substrate 4 with an adhesive layer 32. The substrate 4 is preferably provided with the adhesive layer 32 after it has been provided with an array of holes 40 in a hole making operation. The holes 40 are preferably blind holes with an opening in the proximal surface 61 of the substrate 4.

In embodiments of the invention, the adhesive layer 32 may comprise a silicone based adhesive, acrylic adhesive, or a pressure-sensitive adhesive (PSA) holtmelt. For example, the silicone based adhesive may be a soft silicone gel adhesive which adhesive is known for its advantageous skin friendly properties as inter alia no or little skin is stripped off when an adhesive layer of soft silicone gel adhesive is removed from a dermal surface. The term "silicone gel" refers to a silicone gel that comprises a cross-linked network including silicone of lower molecular weight. For example, suitable soft silicone gel adhesives can be composed of an addition-cured RTV (Room Temperature Vulcanizing) silicone system which, after admixture, crosslinks and forms a self-adhesive elastomer. One example of a commercially available RTV addition-cured silicone system is Wacker SilGel 612 which is a two-component system, wherein the softness and degree of adherence of the formed elastomer can be varied by varying the proportions of the two components A:B from 1.0:0.7 to 1.0:1.3. Other examples of silicone based adhesives include inter alia NuSil MED-6340, NuSil MED3-6300 and NuSil MED 12-6300 from NuSil Technology, Carpinteria, Ga., USA, and Dow Corning 7-9800 from Dow Corning Corporation, Midland, USA. Furthermore, the adhesive layer may have a coating weight of from 20 to 300 $g/m^2$, for example from 50 to 200 $g/m^2$ such as from 80 to 150 $g/m^2$.

The coating operation is in FIG. 3 shown as an application of a transfer paper 31 having a layer of uncured adhesive mixture 34 applied onto the proximal surface 61 of the substrate 4. The transfer paper 31 is, after a curing process, stripped off the proximal surface 61 of the substrate 4, leaving a layer of (cured) adhesive 32 thereon.

The resulting adhesive layer 32 will have through holes 41 in the corresponding positions as the underlying substrate 4 since the adhesive will be drawn in by capillary action into the holes 40 and partly provide a thin adhesive coating on an inner surface of each hole 40. Stated differently, the adhesive layer 32 will slightly extend into the holes 40 and cover the circumferential rims of the holes 40 without entirely blocking the holes. Curing of the adhesive mixture 34 is preferably carried out in an oven with air in the range of 50° to 200° C. Small amounts of the adhesive substance may remain on the transfer paper 31 on the corresponding positions as the underlying holes 40, 41 as the transfer paper 31 is stripped off.

Further details of the coating process and alternative methods for applying an adhesive layer onto a substrate of a wound dressing are readily understood by the skilled artisan, and for example disclosed in EP0855921, by the present applicant, incorporated herein by reference.

Because the adhesive layer 32 will not seal off or close the holes 40, but rather covers a part of the inner walls of each hole 40, more specifically the inner walls of an end portion of the holes that faces the wound when the dressing is worn. Excess wound exudate can still be drawn into the substrate 4 and be retained therein. Similar action will take place in and around any naturally occurring pores that are open up to the proximal surface 61 of the substrate 4 (not shown).

The thickness of the adhesive layer 32 is preferably in the range of 0.1 to 1.0 mm, excluding any penetration into the substrate 4.

Moreover, the substrate 4 functions both as an absorbent and as a carrier for the adhesive layer 32, the dressing 50 as a whole will therefore be very soft and pliant. Because the adhesive layer 32 will adhere to the skin surrounding a wound, the dressing 50 will be held firmly in place while the adhesive layer 32 affords a sealing function and prevents maceration, i.e. prevents wound exudate from reaching healthy surrounding skin. The open structure of the adhesive layer 32 and the substrate 4 also enables the skin to breathe.

Figure 4:
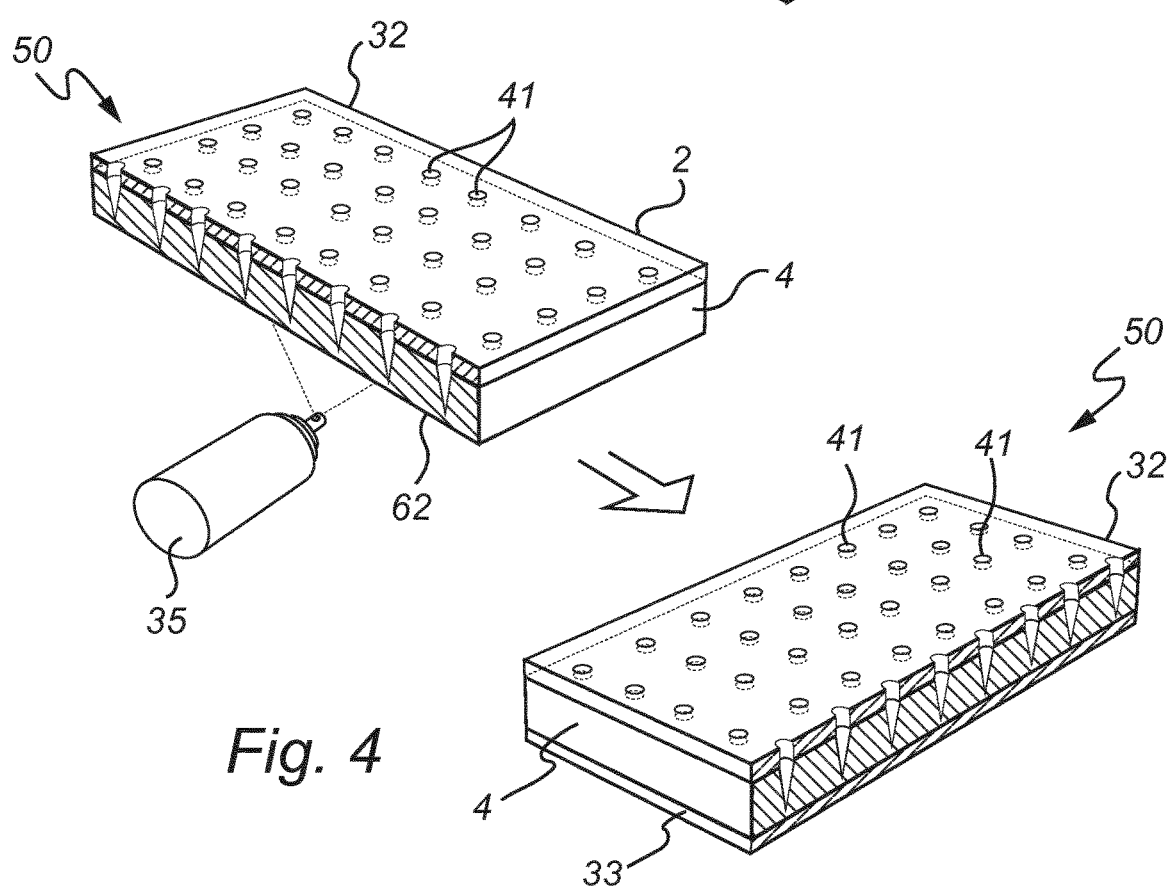
FIG. 4 illustrates a schematic perspective view of a method step for applying a layer of liquid impervious material onto a distal surface of a substrate layer, in accordance with an embodiment of the present invention.

FIG. 4 shows a perspective view of a two-step sequence illustrating a method step of coating the distal surface 62 of the substrate 4 with a backing layer 33. In this particular illustration the backing layer 33 is for illustrative purposes shown as being sprayed onto the distal surface 62 of the substrate 4, however, the backing layer 33 may be applied onto the distal surface 62 by e.g. printing, rolling, or similar. More specifically the step of applying a backing layer may include, by means of a coating means 35, coating the distal surface of the substrate with an (acrylic) adhesive in order to subsequently adhere the backing layer 33 to the substrate 4.

The backing layer 33 is preferably in the form of a thin liquid impervious, but vapour permeable, film or membrane. This is advantageous in order to provide a wound dressing 50 that has a dry outer surface, and to prevent any wound fluid from leaking out of the dressing 50 during use.

The backing layer 33 may be in the form of a film, foil, foam, or membrane. The backing layer may be realized to be pervious to water vapour in accordance to DIN 53333 or DIN 54101.

Preferably, the backing layer 33 may comprise a thermoplastic polymer, for example as a coating, or may consist thereof. A thermoplastic polymer, at first, is to be understood as a polymer that remains thermoplastic if the same is repeatedly heated and cooled within a temperature that is typical for the respective processing or application conditions. Being thermoplastic is understood to be the property of a polymer material to repeatedly soften upon application of heat and to repeatedly harden when cooled down, within a temperature range that is typical for the respective material, wherein the material remains capable of being formed, in the softened stage, and repeatedly, by way of flowing, for example as a shaped article, extruded or otherwise.

Preferred thermoplastic polymers are polyurethane, polyethylene, polypropylene, polyvinyl chloride, polystyrol, polyether, polyester, polyamide, polycarbonate, polyether polyamide copolymers, polyacrylate, polymethacrylate, and/or polymaleate. Preferably, the thermoplastic polymers are elastomeric. It is particularly preferred that the carrier foil comprises thermoplastic polyurethanes (TPU), or consists thereof. Thermoplastic polyurethanes selected from the group comprising aliphatic polyester polyurethanes, aromatic polyester polyurethanes, aliphatic polyether polyurethanes and/or aromatic polyether polyurethanes are particularly suitable. By using these polymers, it is possible to obtain backing layers 33 as breathable elastic membrane films. These are characterized by high flexibility and elasticity over a broad range of temperatures, also having advantageous sealing properties for (liquid) water while having a high water vapour permeability. These materials are further characterized by low noise, advantageous textile feel, resistance against washing and cleaning, very good chemical and mechanical resistance and the fact they are free of plasticizers.

Particularly preferred is also a backing layer 33 that acts as a barrier for germs and has a high sealing capability against exudate emanating from the wound while, at the same time, being permeable for water vapour. In order to achieve the same, the backing layer 33 may, for example, be realized as a semipermeable membrane. The backing layer may be a plastic film, for example, comprising or consisting of polyurethane, polyethylene, or polypropylene. In embodiments of the invention, the backing layer is a polyurethane film having a thickness in the range of 5 to 100 µm, for example, 10 to 80 µm such as 10 to 50 µm, preferably from 10 µm to 30 µm.

The invention has mainly been described above with reference to specific exemplifying embodiments, many different alterations, modifications and the like will become apparent for those skilled in the art. For example, the dressings may further be sterilized, e.g. by ethylene oxide sterilization or steam sterilization, and is intended to be realized in different shapes and sizes suitable for different types of wounds. Furthermore, the illustrated holes have for the sake of convenience been circular, however, other suitable cross-sectional shapes are feasible, e.g. oval, square, rectangular, etc. Moreover, different substances, such as e.g. active carbon, silver, different salts, bactericides, etc., may be mixed into the substrate in order to achieve a desired pharmacological effect. The word "comprising" does not exclude the presence of other elements or steps than those listed in the claim. The word "a" or "an" preceding an element does not exclude the presence of a plurality of such elements.

The invention claimed is:

1. A method for manufacturing a wound dressing having a substrate, said method comprising:
providing a hot pin perforator having an array of heated pins;
providing a sacrificial layer of material adapted to be perforated by the heated pins;
perforating the sacrificial layer with said heated pins; and
making holes in the substrate with the heated pins of said hot pin perforator,
wherein the sacrificial layer does not form a part of the wound dressing during manufacturing,
wherein the substrate comprises an absorbent material.

2. The method according to claim 1, wherein said hot pin perforator is arranged so that the heated pins perforate the sacrificial layer before reaching a proximal surface of the substrate in order to remove residues on the heated pins before they are brought in contact with the substrate.

3. The method according to claim 1, wherein the step of providing a sacrificial layer of material comprises positioning the sacrificial layer of material between said hot pin perforator and the substrate.

4. The method according to claim 1, further comprising:
applying an adhesive layer onto a perforated surface of the substrate.

5. The method according to claim 1, further comprising applying a backing layer onto a distal surface of the substrate, wherein the backing layer comprises a liquid impervious material.

6. The method according to claim 1, wherein the sacrificial layer comprises a material selected from the group consisting of a plastic film, a thin paper material, and a nonwoven material.

7. The method according to claim 1, wherein the heated pins have a temperature at or above the melting point temperature of the substrate.

8. The method according to claim 1, wherein the step of making holes in the substrate, comprises making through holes in the substrate.

9. The method according to claim 1, wherein the step of making holes in the substrate, comprises making blind holes in the substrate.

10. The method according to claim 9, wherein the step of making blind holes in the substrate comprises making blind holes having a depth in the range of 0.2 mm-6.0 mm.

11. The method according to claim 1, wherein the array of heated pins has a pin density in the range of 3-10 pins per $cm^2$.

12. The method according to claim 1, wherein the absorbent material comprises an absorbent foam.

13. The method according to claim 1, wherein the absorbent material comprises an absorbent nonwoven material.

14. The method according to claim 1, wherein the hot pin perforator includes a roller having a plurality of heated pins mounted on an outer surface thereof.

15. The method according to claim 1, further comprising:
providing a supporting surface for the substrate on the opposite sides of the sacrificial layer and the substrate relative to the hot pin perforator, such that the hot pin perforator and the supporting surface form a gap through which the substrate and the sacrificial layer passes.

16. The method according to claim 15, wherein the supporting surface is an outer surface of a counter roller.

17. The method according to claim 15, wherein the sacrificial layer does not contact the substrate during manufacturing.

18. The method according to claim 1, wherein the substrate after manufacturing has an open surface area in the range of 0.1-20%.

19. The method according to claim 1, wherein the absorbent material is selected from the group consisting of a polymeric foam, non-woven material, fibrous material, gel forming fibres, hydrogel, a matrix containing hydrocolloids, woven fibres, and knitted fibres.

\* \* \* \* \*